(12) United States Patent
Wlaschin et al.

(10) Patent No.: US 11,801,231 B2
(45) Date of Patent: *Oct. 31, 2023

(54) ORAL COMPOSITIONS AND METHODS OF USE

(71) Applicant: 3M INNOVATIVE PROPERTIES COMPANY, St. Paul, MN (US)

(72) Inventors: Katie F. Wlaschin, St. Paul, MN (US); Amanda C. Engler, Woodbury, MN (US); Hannah C. Cohen, St. Paul, MN (US); Yizhong Wang, Woodbury, MN (US); Tao Gong, Woodbury, MN (US); Tiffany T. Ton, Woodbury, MN (US); Joel D. Oxman, Minneapolis, MN (US); Jie Yang, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 482 days.

This patent is subject to a terminal disclaimer.

(21) Appl. No.: 16/226,122

(22) Filed: Dec. 19, 2018

(65) Prior Publication Data
US 2019/0365676 A1 Dec. 5, 2019

Related U.S. Application Data

(60) Provisional application No. 62/608,539, filed on Dec. 20, 2017.

(51) Int. Cl.
| | | |
|---|---|---|
| A61K 31/164 | (2006.01) | |
| A61K 9/00 | (2006.01) | |
| A61K 9/107 | (2006.01) | |
| A61K 47/02 | (2006.01) | |
| A61K 47/10 | (2017.01) | |
| A61P 1/02 | (2006.01) | |
| A61K 47/26 | (2006.01) | |
| A61K 47/44 | (2017.01) | |

(52) U.S. Cl.
CPC .......... *A61K 31/164* (2013.01); *A61K 9/0053* (2013.01); *A61K 9/107* (2013.01); *A61K 47/02* (2013.01); *A61K 47/10* (2013.01); *A61K 47/26* (2013.01); *A61K 47/44* (2013.01); *A61P 1/02* (2018.01)

(58) Field of Classification Search
CPC .. A61K 2300/00; A61K 31/05; A61K 31/133; A61K 36/00; A61K 36/28; A61K 31/164; A61K 47/02; A61K 47/10; A61K 47/26; A61K 47/44; A61K 6/20; A61K 6/69; A61K 8/41; A61K 8/922; A61K 9/0053; A61K 9/0056; A61K 9/0095; A61K 9/10; A61K 9/107; A61P 1/02; A61Q 11/00
USPC ....................................................... 514/669
See application file for complete search history.

(56) References Cited

U.S. PATENT DOCUMENTS

| | | | |
|---|---|---|---|
| 2,796,381 A | | 6/1957 | Wilbur |
| 4,971,788 A | | 11/1990 | Tabibi |
| 5,130,122 A | * | 7/1992 | Tabibi ...................... A61K 8/06 |
| | | | 424/49 |
| 5,332,595 A | * | 7/1994 | Gaonkar .............. A23D 7/0053 |
| | | | 426/601 |
| 5,401,496 A | | 3/1995 | Fitzig |
| 5,618,522 A | * | 4/1997 | Kaleta ...................... A61K 8/25 |
| | | | 424/60 |
| 5,624,906 A | | 4/1997 | Vermeer |
| 6,159,459 A | | 12/2000 | Hunter |
| 6,187,323 B1 | | 2/2001 | Aiache |
| 6,596,298 B2 | | 7/2003 | Leung |
| 7,407,669 B2 | | 8/2008 | Leung |

(Continued)

FOREIGN PATENT DOCUMENTS

| | | |
|---|---|---|
| GB | 2139919 | 11/1984 |
| WO | WO 1999-029686 | 6/1999 |

(Continued)

OTHER PUBLICATIONS

Kelly HM, et al. (Bioadhesive, rheological, lubricant and other aspects of an oral gel formulation intended for the treatment of xerostomia. Int J Pharm. Jul. 8, 2004;278(2):391-406. doi: 10.1016/j.ijpharm.2004.03.022. PMID: 15196643.).*

Kelly, et al., "Bioadhesive Rheological, Lubricant and other Aspects of an Oral Gel Formulation Intended for the Treatment of Xerostomia," Jan. 22, 2004, pp. 391-406. International Journal of Pharmaceutics 278 (2004).

(Continued)

*Primary Examiner* — Lakshmi S Channavajjala
(74) *Attorney, Agent, or Firm* — 3M Innovative Properties Company

(57) ABSTRACT

Compositions that include from 0.1 wt-% to 8 wt-% of one or more compounds of formula (I) based on the total weight of the composition $$HOCH_2-(CHOH)_n-CH_2NR^1R^2 \qquad (I)$$

wherein $R^1$ and $R^2$ are independently selected from the group consisting of a hydrogen atom, an alkyl group, $C(O)R^3$, and $SO_2R^4$; with $R^3$ and $R^4$ being independently selected from the group consisting of an alkyl group, an aryl group, and an aralkyl group; wherein n is an integer from about 2 to about 5; from 5 wt-% to 95 wt-% of one or more plant based oils based on the total weight of the composition; from 5 wt-% to 80 wt-% water based on the total weight of the composition and from 0.01 wt-% to 1 wt-% of one or more nonionic aromatic phenolic preservatives based on the total weight of the composition wherein the composition has a pH from 4.5 to 9.5, the composition is an emulsion, and the composition is edible.

19 Claims, No Drawings

(56) References Cited

U.S. PATENT DOCUMENTS

| | | | |
|---|---|---|---|
| 7,867,509 B2 | 1/2011 | Leung | |
| 8,367,650 B2 | 2/2013 | Desjonqueres | |
| 8,460,689 B2* | 6/2013 | Wlaschin | A61P 17/00 424/405 |
| 8,540,970 B2 | 9/2013 | Rodriguez-Vilaboa | |
| 8,647,608 B2 | 2/2014 | Yang | |
| 8,808,722 B2* | 8/2014 | Scholz | A61K 31/13 424/422 |
| 8,968,709 B2 | 3/2015 | Yang | |
| 9,289,369 B2 | 3/2016 | Boyd | |
| 9,717,667 B2 | 8/2017 | Patel | |
| 9,724,278 B2 | 8/2017 | Lambert | |
| 11,324,681 B2* | 5/2022 | Wlaschin | A61K 9/006 |
| 2006/0263412 A1 | 11/2006 | Pan | |
| 2007/0031561 A1 | 2/2007 | Lakkis | |
| 2007/0154411 A1* | 7/2007 | Barth | A61Q 11/02 424/50 |
| 2007/0183985 A1 | 8/2007 | Tallia | |
| 2007/0190090 A1 | 8/2007 | Brown | |
| 2008/0020024 A1 | 1/2008 | Kulkarni | |
| 2009/0311200 A1 | 12/2009 | Lambert | |
| 2010/0150847 A1 | 6/2010 | Yang | |
| 2010/0285148 A1* | 11/2010 | Wlaschin | A61P 17/00 424/616 |
| 2013/0052146 A1 | 2/2013 | Yang | |
| 2013/0269133 A1 | 10/2013 | Ontumi | |
| 2014/0155457 A1* | 6/2014 | Nho | A61K 31/77 514/425 |
| 2014/0322147 A1 | 10/2014 | Modak | |
| 2016/0213001 A1 | 7/2016 | Parthasarathy | |
| 2016/0374352 A1 | 12/2016 | Modak | |
| 2017/0252293 A1 | 9/2017 | Brumbaugh | |
| 2019/0083220 A1* | 3/2019 | Wlaschin | A61K 8/731 |
| 2020/0330347 A1* | 10/2020 | Wlaschin | A61K 8/678 |

FOREIGN PATENT DOCUMENTS

| | | |
|---|---|---|
| WO | WO 2004/096192 | 11/2004 |
| WO | WO 2009/014907 | 1/2009 |
| WO | WO 2010/129795 A1 | 11/2010 |
| WO | WO 2012-087279 | 6/2012 |
| WO | WO 2012-087280 | 6/2012 |
| WO | WO 2012-087281 | 6/2012 |
| WO | WO 2014/098868 | 1/2014 |
| WO | WO 2014-151567 | 9/2014 |
| WO | WO 2014-165226 | 10/2014 |
| WO | WO 2017/205230 | 11/2017 |

OTHER PUBLICATIONS

Kelly, "Bio adhesive, rheological, lubricant and other aspects of an oral gel formulation intended for the treatment of xerostomia" International journal of pharmaceutics, 2004, vol. 278, pp. 391-406.

Zhang, "Food-grade filled hydrogels for oral delivery of lipophilic active ingredients: Temperature-triggered release microgels", Food Research International, 2015, vol. 69, pp. 274-280.

International Search Report for PCT International Application No. PCT/IB2018/060108, dated Mar. 22, 2019, 5 pages.

* cited by examiner

ORAL COMPOSITIONS AND METHODS OF USE

TECHNICAL FIELD

The present disclosure relates to oral compositions, and more specifically oral compositions and methods to relieve xerostomia and improve oral health of a subject.

BACKGROUND

Xerostomia or dry mouth is a common condition that results from insufficient saliva volume. It is increasingly prevalent in the aging population and is a side-effect of many medications, as well as cancer treatment. Severe cases of xerostomia are often related to salivary gland dysfunction, known as Sjögren's Syndrome.

The lack of moisture and lubrication typically provided by saliva has a range of negative effects on oral tissue (soft tissue) ranging from mild discomfort to extremely painful and infected mouth sores. The persistent discomfort and dryness can also contribute to larger health issues by causing disruption of sleep, and impairing one's ability to talk (socialize, may impact psychological health) and eat (may impact nutrition). Dry buccal tissue is a less effective barrier and more susceptible to penetration by physical irritants such as toxins and carcinogens in foods, beverages and tobacco. There remains a need for compositions which provide improved relief for xerostomia.

SUMMARY

Disclosed herein are compositions that include from 0.1 wt-% to 8 wt-% of one or more compounds of formula (I) based on the total weight of the composition

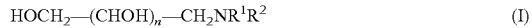

$$HOCH_2-(CHOH)_n-CH_2NR^1R^2 \quad (I)$$

wherein $R^1$ and $R^2$ are independently selected from the group consisting of a hydrogen atom, an alkyl group, $C(O)R^3$, and $SO_2R^4$; with $R^3$ and $R^4$ being independently selected from the group consisting of an alkyl group, an aryl group, and an aralkyl group; wherein n is an integer from about 2 to about 5; from 5 wt-% to 95 wt-% of one or more plant based oils based on the total weight of the composition; from 5 wt-% to 80 wt-% water based on the total weight of the composition, and not greater than 1 wt-% of one or more nonionic aromatic phenolic preservatives based on the total weight of the composition wherein the composition has a pH from 4.5 to 9.5, the composition is an emulsion, and the composition is edible.

Also disclosed are methods of preventing, inhibiting, disrupting, dispersing, reducing or any combination thereof the formation or maintenance of a biofilm in an oral tissue, the methods including contacting an oral tissue with disclosed compositions.

Also disclosed are methods of affecting hydration loss in an oral tissue, the methods including contacting an oral tissue with disclosed compositions.

Also disclosed are methods of affecting lubricity or lubriciousness in an oral tissue, the methods including contacting an oral tissue with disclosed compositions.

Also disclosed are methods of affecting the effects of xerostomia, dry mouth, or both, the methods including contacting an oral tissue with disclosed compositions.

The above summary is not intended to describe each embodiment of the present disclosure. The details of one or more embodiments of the present disclosure are also set forth in the description below. Other features, objects, and advantages of the present disclosure will be apparent from the description and from the claims.

DETAILED DESCRIPTION

Saliva is also the mouth's primary defense against tooth decay. Healthy saliva flow helps prevent cavities by physically removing bacteria from the oral cavity before they can become attached to tooth and tissue surfaces and form a protected biofilm. The flow of saliva also helps dilute sugars and acids introduced by intake of food and beverages. The buffering capacity neutralizes acids and aids in the digestive process. The presence of calcium and phosphate salts provides continuous opportunity for re-mineralization of tooth enamel, serving to reverse the tooth decay process.

Many who suffer with xerostomia use separate products to address hard tissue health and soft tissue comfort. For soft tissue comfort, saliva substitute products are typically designed to provide lubrication and moisture. The format of these products is varied, and includes viscous gels/pastes, sprays, rinses, mints, and slow-release tablets. These are applied multiple-times per day or as needed for comfort. For hard-tissue health, different treatments are used to directly address cavity prevention (antiseptic rinses, fluoride products, calcium/phosphate treatments). Often "dry mouth friendly" versions of products, such as toothpastes and mouth rinses are recommended. Dry mouth friendly products typically have a neutral pH and do not contain alcohol or other irritating components (e.g. anionic surfactants or emulsifiers).

There is a desire to design a single product that effectively addresses both the need for dry mouth symptom relief (soft tissue comfort) and oral health preventative benefits (tooth enamel and cavity protection). A fully ingestible, two-phase emulsion system is well suited for this purpose. It addresses both the health of hard-tissue (water phase) and the comfort of soft tissue (oil phase).

Disclosed herein are compositions that can be utilized as oral compositions, for example. Compositions disclosed herein can include water-in-oil (w/o) emulsions and oil-in-water (o/w) emulsions. A w/o (water-in-oil) emulsion consists of water droplets dispersed in a continuous oil phase. In some embodiments, useful compositions can be characterized as a macroemulsion. Macroemulsions are kinetically stabilized mixtures of at least two immiscible liquids where one of the liquids has droplets with a diameter greater than 0.1 μm. Macroemulsions scatter light effectively and therefore appear milky, because their droplets are greater than a wavelength of light.

Disclosed compositions, one or more components in a composition, or both can be characterized as edible. Referring to a component or composition as edible can mean that the particular ingredient or composition is safe for daily, long-term ingestion at recommended use levels. In some embodiments, the GRAS (generally regarded as safe) list from the United States Food and Drug Administration (FDA) can be utilized to determine if a component is edible at the levels utilized in a composition.

Disclosed compositions include at least oil, at least one surfactant according to formula I, and at least one preservative. The amount of water in disclosed compositions can be characterized by the amount of aqueous phase in the composition. The aqueous phase can include components other than water, for example it can include components that are soluble in water (as opposed to the oil phase). In some embodiments, the aqueous phase can be not greater than 95 percent by weight (wt-%) based on the total weight of the composition, not greater than 30 wt-% based on the total weight of the composition, or not greater than 5 wt-% based on the total weight of the composition.

Disclosed compositions also include one or more oils. Useful oils can include any oils but in some embodiments can include plant based oils. For example, plant based oils can be extracted from various plants (e.g., soybean, canola, and chili), seeds (e.g., sesame and sunflower), nuts (e.g., walnut and macadamia), and fruits (e.g., palm, olive, and coconut), for example. In some embodiments, useful oils can include one or more than one that are liquids at room temperature. The composition can include a single edible oil, or as many as two, three, four, five or more edible oils. Examples of suitable edible oils can include, but are not limited to, sunflower oil (including high oleic sunflower oil), safflower oil (including high oleic safflower oil), olive oil, coconut oil, palm oil, peanut oil, soybean oil, linseed oil, rapeseed oil, flaxseed oil, hempseed oil, cocoa butter, walnut oil, corn oil, grape seed oil, sesame oil, groundnut oil, wheat germ oil, cottonseed oil, fish oil, watermelon seed oil, lemon oil, orange oil, thistle oil, tomato seed oil, almond oil, perilla oil, canola oil, pistachio oil, hazelnut oil, avocado oil, camellia seed oil, shea nut oil, macadamia nut oil, apricot kernel oil, oleic acid, ozonated oils, and the like, and mixtures or fractions thereof.

Disclosed compositions can include not greater than 95 wt-% of one or more oils based on the total weight of the composition, not greater than 90 wt-% of one or more oils based on the total weight of the composition, or not greater than 89 wt-% of one or more oils based on the total weight of the composition. Disclosed compositions can include not less than 5 wt-% of one or more oils based on the total weight of the composition, not less than 30 wt-% of one or more oils based on the total weight of the composition, or not less than 50 wt-% of one or more oils based on the total weight of the composition.

Disclosed compositions also include one or more compounds of formula I:

$$HOCH_2\text{---}(CHOH)_n\text{---}CH_2NR^1R^2 \qquad (I)$$

wherein $R^1$ and $R^2$ are independently selected from the group consisting of a hydrogen atom, an alkyl group, $C(O)R^3$, and $SO_2R^4$; with $R^3$ and $R^4$ being independently selected from the group consisting of an alkyl group, an aryl group, and an aralkyl group; wherein n is an integer from about 2 to about 5.

The groups $R^1$ and $R^2$ are independently selected from the group consisting of a hydrogen atom, an alkyl group, $C(O)R^3$, and $SO_2R^4$. Each of $R^1$ and $R^2$ may be a hydrogen atom, each of $R^1$ and $R^2$ may be an alkyl group, each of $R^1$ and $R^2$ may be $C(O)R^3$, or each of $R^1$ and $R^2$ may be $SO_2R^4$. In some embodiments, $R^1$ may be a hydrogen atom and $R^2$ may be an alkyl group, $C(O)R^3$, or $SO_2R^4$. In other embodiments, $R^1$ may be an alkyl group, and $R^2$ may be $C(O)R^3$, or $SO_2R^4$. In still other embodiments, $R^1$ may be $C(O)R^3$, and $R^2$ may be $SO_2R^4$. When either or both of $R^1$ and $R^2$ is an alkyl group, the alkyl group may comprise about one carbon atom, more than about one carbon atom, more than about two carbon atoms, more than about four carbons atoms, more than about six carbon atoms, more than about eight carbon atoms, more than about ten carbon atoms, more than about twelve carbon atoms, more than about fourteen carbon atoms, more than about sixteen carbon atoms, or more than about eighteen carbon atoms. In some embodiments, the alkyl group comprises less than about thirty carbon atoms, less than about twenty-six carbon atoms, or less than about twenty carbon atoms. In some embodiments, the alkyl group comprises a straight chain alkyl group. In other embodiments, the alkyl group comprises a branched alkyl group. In still other embodiments, the alkyl group comprises a cyclic alkyl group. When each of $R^1$ and $R^2$ comprises an alkyl group, $R^1$ and $R^2$ may comprise the same alkyl group, or $R^1$ and $R^2$ may comprise different alkyl groups. Non-limiting examples of alkyl groups include methyl, ethyl, 1-propyl, iso-propyl, butyl, iso-butyl, sec-butyl, pentyl, iso-pentyl, neo-pentyl, hexyl, 2-ethylhexyl, octyl, decyl, undecyl, dodecyl, tetradecyl, pentadecyl, octadecyl, cyclohexyl, 4-methylcyclohexyl, cyclohexylmethyl, cyclopenyl, and cyclooctyl.

The groups $R^3$ and $R^4$ are independently selected from the group consisting of an alkyl group, an aryl group, and an aralkyl group. When either or both of $R^3$ or $R^4$ is an alkyl group, the alkyl group may comprise about one carbon atom, more than about one carbon atom, more than about two carbon atoms, more than about four carbons atoms, more than about six carbon atoms, more than about eight carbon atoms, more than about ten carbon atoms, more than about twelve carbon atoms, more than about fourteen carbon atoms, more than about sixteen carbon atoms, or more than about eighteen carbon atoms. In some embodiments, the alkyl group comprises less than about thirty carbon atoms, less than about twenty-six carbon atoms, or less than about twenty carbon atoms. In some embodiments, the alkyl group comprises a straight chain alkyl group. In other embodiments, the alkyl group comprises a branched alkyl group. In still other embodiments, the alkyl group comprises a cyclic alkyl group. In compounds of Formula I or pharmaceutically acceptable salts thereof, when both $R^3$ and $R^4$ groups are present, and when each of $R^3$ and $R^4$ comprises an alkyl group, $R^3$ and $R^4$ may comprise the same alkyl group, or $R^3$ and $R^4$ may comprise different alkyl groups. Non-limiting examples of alkyl groups include methyl, ethyl, 1-propyl, iso-propyl, butyl, iso-butyl, sec-butyl, pentyl, iso-pentyl, neo-pentyl, hexyl, 2-ethylhexyl, octyl, decyl, undecyl, dodecyl, tetradecyl, pentadecyl, octadecyl, cyclohexyl, 4-methylcyclohexyl, cyclohexylmethyl, cyclopenyl, and cyclooctyl.

When either or both of $R^3$ or $R^4$ are an aryl group, the aryl group may comprise one arene ring or more than one arene ring. Arene rings may comprise up to six carbon atoms, up to eight carbon atoms, up to ten carbon atoms, up to twelve carbon atoms, up to fourteen carbon atoms, up to sixteen carbon atoms, or up to eighteen carbon atoms. Arene rings may comprise a heteroatom, for example, nitrogen, oxygen, or sulfur. If more than one arene ring is present, the arene rings may be fused together, or they may be joined by a chemical bond. In compounds of Formula I or pharmaceutically acceptable salts thereof, when both $R^3$ and $R^4$ groups are present, and when each of $R^3$ and $R^4$ comprises an aryl group, $R^3$ and $R^4$ may comprise the same aryl group, or $R^3$ and $R^4$ may comprise different aryl groups. Non-limiting examples of aryl groups include substituted and unsubstituted phenyl, 1-naphthyl, 2-naphthyl, 9-anthracenyl.

When either or both of $R^3$ or $R^4$ are an aralkyl group, the aralkyl group may comprise one arene ring or more than one arene ring. The aralkyl group may comprise up to six carbon atoms, up to eight carbon atoms, up to ten carbon atoms, up to twelve carbon atoms, up to fourteen carbon atoms, up to sixteen carbon atoms, up to eighteen carbon atoms, or up to twenty carbon atoms. If more than one arene ring is present in the aralkyl group, the arene rings may be fused together, or they may be joined by a chemical bond. Arene rings may comprise a heteroatom, for example, nitrogen, oxygen, or sulfur. In compounds of Formula I or pharmaceutically acceptable salts thereof, when both $R^3$ and $R^4$ groups are present, and when each of $R^3$ and $R^4$ comprises an aralkyl group, $R^3$ and $R^4$ may comprise the same aralkyl group, or $R^3$ and $R^4$ may comprise different aralkyl groups. Non-limiting examples of aralkyl groups include benzyl, 1-phenylethyl, 2-phenylethyl, 3-phenylpropyl, 2-naphthylethyl, and 9-anthracenylmethyl.

In Formula I, n is an integer from about 2 to about 5. In some embodiments, the composition comprises a compound of Formula I, or a pharmaceutically acceptable salt thereof, wherein n is an integer having a value of about 5, about 4, about 3, or about 2. In some embodiments, n is an integer having a value of 5, or 4, or 3, or 2. It is understood that the composition may comprise more than one compound of Formula I, or a pharmaceutically acceptable salt thereof, and that the compounds may be represented by Formula I with different integer values of n. In these embodiments, the average value of n of a composition may be a non-integer.

Pharmaceutically acceptable salts include ammonium salts. In some embodiments, the composition of the invention comprises an ammonium salt. An ammonium salt may be represented as the reaction product of an acid with an amine, or as the reaction product of an amine with an alkylating agent such as, for example, iodomethane, bromoethane, or benzyl bromide. An ammonium salt includes a protonated amine compound, for example a compound of Formula I in which a $NR^1R^2$ group, wherein $R^1$ and $R^2$ are independently selected from the group consisting of a hydrogen atom and an alkyl group, has been protonated with an inorganic acid or an organic acid. An ammonium salt includes an alkylated amine compound, for example a compound of Formula I in which a $NR^1R^2$ group, wherein $R^1$ and $R^2$ are independently selected from the group consisting of a hydrogen atom and an alkyl group, has been alkylated with an alkylating agent.

An ammonium salt comprises at least one counter ion that may be an inorganic anion, an organic anion, or a combination of anions. A combination of anions includes a combination of more than one inorganic anion, a combination of more than one organic anion, or a combination of an inorganic ion and an organic anion. Inorganic ions include, for example, halide (fluoride, chloride, bromide, and iodide), nitrate, sulfate, tetrafluoroborate, and tetra(aryl)borates. Tetra(aryl)borates include compounds having the formula $Z_4B^-$, where Z is an aromatic group, for example a substituted or unsubstituted phenyl group. Examples of tetra(aryl)borates include, but are not limited to, tetraphenylborate, tetrakis(4-methylphenyl)borate, tetrakis(2-methylphenyl)borate, tetrakis(1,3,5-trimethylphenyl)borate, tetrakis(4-fluorophenyl)borate, tetrakis(pentafluorophenyl)borate, and tetrakis(4-trifluoromethylphenyl)borate. Organic anions include, for example, alkanoates (such as, for example, acetate, propionate, and butanoate), benzoate, fumarate, maleate, tartrate, ascorbate, benzenesulfonate, toluenesulfonate, and citrate. In some embodiments, the pharmaceutically acceptable salt is free of unsubstituted or substituted tropolone.

In certain implementations, an ammonium salt may be formed by protonation of a compound of Formula I, wherein $R^1$ and $R^2$ are independently selected from a hydrogen atom and an alkyl group, with an inorganic acid, an organic acid, or a combination of an inorganic acid and an organic acid. In another embodiment, an ammonium salt may be formed by alkylation of a compound of Formula I, wherein $R^1$ and $R^2$ are independently selected from a hydrogen atom and an alkyl group, with an alkylating agent. In yet another embodiment, an ammonium salt may be formed by an ion exchange or metathesis reaction with a previously formed ammonium salt.

In some embodiments, $R^1$ and $R^2$ are each a hydrogen atom. In some embodiments, pharmaceutically acceptable salts comprise ammonium halides. In certain embodiments, the composition comprises a compound of Formula II or a pharmaceutically acceptable salt thereof. In some embodiments, the salt comprises an ammonium halide. In a specific embodiment, the ammonium halide comprises an ammonium chloride.

$$HOCH_2—(CHOH)_4—CH_2NH_2 \qquad (II)$$

In some embodiments, $R^1$ comprises an alkyl group and $R^2$ is $C(O)R^3$, where $R^3$ comprises an alkyl group. In certain embodiments, $R^1$ comprises an alkyl group having from about one to about four carbon atoms, and $R^3$ comprises an alkyl group having from about four to about sixteen carbon atoms. In some embodiments, $R^1$ comprises a methyl group, and $R^3$ comprises an alkyl group having seven, eight, or nine carbon atoms. In some embodiments, the composition comprises a compound of Formula III, Formula IV, or Formula V.

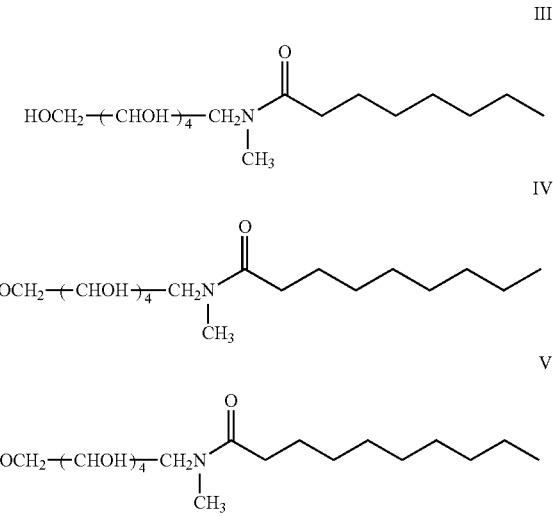

In some embodiments, $R^1$ is a hydrogen atom and $R^2$ comprises an alkyl group. In some embodiments pharmaceutically acceptable salts comprise ammonium halides. In some embodiments, the alkyl group comprises from about one to about eight carbon atoms. In certain embodiments, the dental composition comprises a compound of Formula VI or a pharmaceutically acceptable salt thereof. The salt may comprise an ammonium halide. In some embodiments, the ammonium halide comprises an ammonium chloride. In certain embodiments, the dental composition comprises a compound of Formula VII or a pharmaceutically acceptable salt thereof. The salt may comprise an ammonium halide. In some embodiments, the ammonium halide comprises an ammonium chloride. In some embodiments, $R^1$ and $R^2$ independently comprise an alkyl group having from about one to about eight carbon atoms. In certain embodiments, the dental composition comprises a compound of Formula VIII or a pharmaceutically acceptable salt thereof. The salt may comprise an ammonium halide. In some embodiments, the ammonium halide comprises an ammonium chloride.

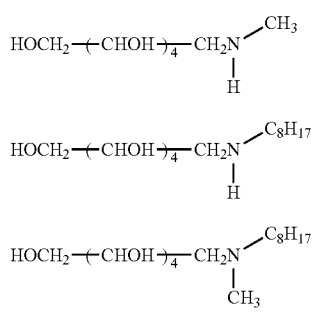

It is recognized that the compounds of Formulae comprise chiral carbon atoms. For simplicity, in Formulae the stereochemical configuration about each of the chiral carbon atoms is not specified. It is intended that Formula I-VIII, as used in this description and in the claims, represents each of the compounds having any of the possible stereochemical configurations. In some embodiments, the compounds of Formulae II though VIII are amino sugar alcohols and derivatives having the common names D-glucamine, N-methyl-N-octanoyl-D-glucamine ("MEGA-8"), N-methyl-N-nonanoyl-D-glucamine ("MEGA-9"), N-methyl-N-decanoyl-D-glucamine ("MEGA-10"), N-methyl-D-glucamine, N-octyl-D-glucamine, and N-methyl-N-octyl-D-glucamine, respectively.

Disclosed compositions can include not greater than 8 wt-% of one or more compounds of formula I based on the total weight of the composition, not greater than 7 wt-% of one or more compounds of formula I based on the total weight of the composition, or not greater than 6 wt-% of one or more compounds of formula I based on the total weight of the composition. In some embodiments, disclosed composition can include not less than 0.1 wt of one or more compounds of formula I based on the total weight of the composition, not less than 1 wt-% of one or more compounds of formula I based on the total weight of the composition, not less than 2 wt-% of one or more compounds of formula I based on the total weight of the composition, or not less than 4 wt-% of one or more compounds of formula I based on the total weight of the composition.

Disclosed compositions also include one or more than one preservative. Illustrative useful preservatives can include nonionic aromatic phenolic preservatives. Specific illustrative useful preservatives can include propyl paraben, thymol, a mixture of gluconolactone and sodium benzoate (such as GEOGARD ECT™ from Lonza Group Ltd, Switzerland).

Disclosed compositions can include not greater than 0.8 wt-% of one or more nonionic aromatic phenolic preservatives based on the total weight of the composition, not greater than 0.6 wt-% of one or more nonionic aromatic phenolic preservatives based on the total weight of the composition, or not greater than 0.1 wt-% of one or more nonionic aromatic phenolic preservatives based on the total weight of the composition. In some embodiments, disclosed composition can include not less than 0.1 wt of one or more nonionic aromatic phenolic preservatives based on the total weight of the composition, not less than 0.6 wt-% of one or more nonionic aromatic phenolic preservatives based on the total weight of the composition, or not less than 0.8 wt-% of one or more nonionic aromatic phenolic preservatives based on the total weight of the composition.

Disclosed compositions can also optionally include additional components other than those above. Illustrative optional components can include, for example, sweeteners, humectants, mineral salts, buffering components, flavorants, preservative agents, prebiotics, probiotics, or combinations thereof. Other optional beneficial ingredients can also be included at appropriate levels such as, aloe vera (multi-benefit), folic acid (related to B12), hyaluronic acid (lubricating, healthy skin), octyl glucopyranoside, N-acetyl-D-glucosamine, N-acetyl-D-Galactosamine, D-glucosamine hydrochloride, D-glucosamine sulfate, D-glucamine, N-methyl-D-glucamine, N-ethyl-D-glucamine, N-octyl-D-glucamine, glycine, nonanoic acid, ethyl caprylate, DMSO, ceramides (healthy skin), arginine, betaines or oxygenated glycerol triesters, vitamin E (antioxidant and preservative), vitamin B12 (healthy skin, etc.), EDTA, cetyl pyridinium chloride, chlorhexidine, other antiseptics, etc., or combinations thereof.

In some embodiments, disclosed compositions can include flavorants including for example, peppermint, strawberry, butter, vanilla, coconut, almond, bubble gum, berry, fruit punch, butterscotch, caramel, or combinations thereof. In some embodiments, some flavorants, e.g., mint, citrus, etc. can also be advantageous because they stimulate salivary production when utilized in compositions. Artificial sweeteners may also be used (stevia, aspartame, sucralose, neotame, acesulfame potassium (Ace-K), saccharin, and advantame, for example). In some embodiments, disclosed compositions can include one or more sweeteners including for example, non-cariogenic polyols, or sugar substitutes (e.g., sucralose). In some embodiments, disclosed compositions can include non-cariogenic polyol sweeteners such as xylitol, sorbitol, maltitol, erythritol, mannitol, isomalt, or combinations thereof. In compositions that include optional sweeteners, the sweetener can be present in an amount that is not less than 1 wt-% based on the total weight of the composition or not less than 0.5 wt-% based on the total weight of the composition. In some embodiments, an optional sweetener can be present in an amount that is not greater than 25 wt-% based on the total weight of the composition or not greater than 20 wt-% based on the total weight of the composition or not greater than 15 wt-% based on the total weight of the composition.

In some embodiments, disclosed compositions can include one or more humectants including for example glycerin, propylene glycol, or sucrose, or combinations thereof. In some embodiments, disclosed compositions can include glycerin as a humectant. In compositions that include optional humectants, the one or more humectant can be present in an amount of not less than 2.5 wt-% based on the total weight of the composition, not less than 5 wt-% based on the total weight of the composition, or not less than 10 wt-% based on the total weight of the composition. In compositions that include optional humectants, the one or more humectant can be present in an amount of not greater than 40 wt-% based on the total weight of the composition, not greater than 60 wt-% based on the total weight of the composition, or not greater than 80 wt-% based on the total weight of the composition.

In some embodiments, disclosed compositions can optionally include one or more minerals that may be useful or beneficial for ingestion or oral health. Illustrative optional minerals that can be included in disclosed compositions can include calcium (Ca), phosphorus (P), magnesium (Mg), fluorine (F), iron (Fe), strontium (Sr), zinc (Zn), potassium (K), or combinations thereof. In some embodiments, some minerals can be provided by including magnesium chloride (MgCl$_2$), calcium chloride (CaCl$_2$)), strontium chloride, zinc chloride, zinc gluconate, potassium nitrate, potassium phosphate dibasic (KH$_2$PO$_4$), or combinations thereof. In some embodiments, where fluorine is included, it can be included as the fluoride ion (F—) in salt form (MgF$_2$, CaF$_2$, etc.).

In some embodiments, disclosed compositions can include one or more preservatives to render the composition microbiologically stable, to increase the microbiological stability thereof, or some combination thereof. In some embodiments, useful preservatives include those that work at a neutral pH, do not detrimentally affect taste, are edible, are effective against a broad spectrum of pathogens, or combinations thereof. Specific illustrative useful preservatives can include GEOGARD® preservatives, which are commercially available from Lonza (Basel, Switzerland) and include salicylic acid, benzyl alcohol, sodium benzoate, potassium sorbate, parabens, natural preservatives, polyglyceryl esters, monolaurin, 1,2 octanediol, caprylic/capric triglycerides, DHA, aloe vera, potassium sorbate, CPC, PHMB, CHG, vitamin E, triethyl citrate, and EDTA, for example. Specific examples of GEOGARD preservatives include: GEOGARD ECT [benzyl alcohol (77-86%), salicylic acid (8-15%), glycerin (3-5%), and sorbic acid (1-4%)]; and GEOGARD 221 [dehydroacetic acid (7.7-8.3%), benzyl alcohol (85-89%), and water (4%)]

In some embodiments, disclosed compositions can include one or more naturally occurring amino acids as agents to aid in the prevention of dental caries. Dental "caries" is understood as tooth decay, which leads to tooth demineralization. The following amino acids were found to be useful as dental caries preventing agents: glycine, leucine, isoleucine, lysine, methionine, phenylalanine, serine, threonine, valine, tryptophan and mixtures thereof; with the following amino acids being sometimes preferred: glycine, phenylalanine, serine, isoleucine, leucine, methionine; with glycine and phenylalanine being sometimes being even more preferred. The amino acids may be natural or synthetic. The amino acids might be in D- or L-configuration. In some embodiments the L-configuration is preferred.

In some embodiments, disclosed compositions can include the amino acids present in the following amounts (wt. % with respect to the weight of the whole composition): at least 0.1, or at least 1, or at least 2 wt. %. In some embodiments, disclosed compositions can include the amino acids present in the following amounts (wt. % with respect to the weight of the whole composition): not more than 15 or not more than 12 or not more than 10 wt. %. In some embodiments, disclosed compositions can include the amino acids present in the following amounts (wt. % with respect to the weight of the whole composition), in a range including and between 0.1 to 15, or a range including and between 1 to 12, or a range including and between 2 to 10 wt. %.

In some embodiments, disclosed compositions include the following concentration of the amino acid, alone or in combination with other amino acids: glycine in an amount of 0.1 to 10 wt. %; or leucine in an amount of 0.1 to 5 wt. %; or isoleucine in an amount of 0.1 to 5 wt. %; or lysine in an amount of 0.1 to 10 wt. %; or methionine in an amount of 0.1 to 10 wt. %; or phenylalanine in an amount of 0.1 to 5 wt. %; or serine in an amount of 0.1 to 10 wt. %; or threonine in an amount of 0.1 to 10 wt. %; or valine in an amount of 0.1 to 8 wt. %; or tryptophan in an amount of 0.1 to 2 wt. %; all of the above in wt. % with respect to the weight of the whole composition.

In some embodiments, disclosed compositions include the following concentration of the amino acid, alone or in combination with other amino acids: glycine in an amount of 1 to 10 wt. %; or leucine in an amount of 1 to 5 wt. %; or isoleucine in an amount of 2 to 5 wt. %; or lysine in an amount of 5 to 10 wt. %; or methionine in an amount of 2 to 10 wt. %; or phenylalanine in an amount of 1 to 5 wt. %; or serine in an amount of 1 to 10 wt. %; or threonine in an amount of 6 to 10 wt. %; or valine in an amount of 3 to 8 wt. %; or tryptophan in an amount of 0.5 to 2 wt. %; all of the above in wt. % with respect to the weight of the whole composition In contrast, the following amino acids were found to be not effective for caries prevention: proline, arginine, histidine, aspartic acid, glutamine, tyrosine. Some embodiments of the disclosed composition do not contain these amino acids: proline, arginine, histidine, aspartic acid, glutamine, tyrosine. Some embodiments of the disclosed composition contain these amino acids in only in an amount of not more than 0.5 wt. %, or more than 0.3 wt. %, or more than 0.1 wt. % with respect to the weight of the whole composition.

In some embodiments, disclosed compositions do not include any quaternary ammonium compounds.

Disclosed compositions can have varied properties. In some embodiments, disclosed compositions can be described by the pH thereof, the viscosity thereof, the stability thereof, various other properties, or combinations thereof.

In some embodiments, disclosed compositions can have a pH that is acceptable for use in the mouth of a person, for example. In some embodiments, disclosed compositions can have a pH from 4.5 to 9.5, for example. In some embodiments, the composition can have a pH in a more neutral range from 5.0-8.5 or 5.5-8.5 for example, as dry mouth sufferers can have a higher sensitivity to pH. The composition can naturally have such a pH or can be buffered to have a pH in a useful, e.g., a "neutral" range.

In some embodiments, disclosed compositions can optionally include one or more acid neutralization/buffering agents that may be useful or beneficial for oral health to reduce teeth acid erosion. Such compositions may have the capability to buffer or neutralize acid in oral cavity to reduce acid erosion.

In some embodiments, the acid buffering agent can include any basic substance which dissociates in water (e.g., an aqueous base) to produce one or more hydroxyl ions, or any substance which can accept a proton, or which has an unshared pair of electrons.

In some embodiments, the acid buffering or neutralizing agent can include carbonates, bicarbonates, chlorides, hydroxides, dibasic citrates phosphates, sulfates and the like, typically in the form of a salt. Illustrative salts include a complex with sodium, potassium, calcium, ammonium, aluminum, magnesium, and the like. In some other embodiments, the acid buffering agent can include sodium carbonate, potassium carbonate, calcium carbonate, ammonium bicarbonate, ammonium carbonate, ammonium chloride, ammonium hydroxide, dibasic ammonium citrate, ammonium phosphate (monobasic or dibasic), ammonium sulfate, aluminum carbonate, aluminum hydroxide, calcium citrate, calcium hydroxide, magnesium carbonate, magnesium hydroxide, magnesium phosphate (dibasic), potassium hydroxide, potassium bicarbonate, and the like.

In some embodiments, the acid buffering or neutralizing agent can include phosphate based buffers which contain PO$_4^{3-}$ anion (e.g., sodium phosphate, potassium phosphate, calcium phosphate and ammonium phosphate), hydrogen phosphate based buffers which contain HPO$_4^{2-}$ anion (e.g., sodium hydrogen phosphate, potassium phosphate and calcium phosphate), dihydrogen phosphate based buffers which contain $H_2PO_4^-$ anion (e.g., sodium dihydrogen phosphate, potassium dihydrogen phosphate and calcium dihydrogen phosphate), carboxylates based buffers which contain $RCOO^-$ anion (e.g., sodium acetate, sodium citrate, potassium acetate, ammonium acetate and ammonium citrate), carbonate based buffers which contain $CO_3^{2-}$ anion (e.g., sodium carbonate, calcium carbonate, magnesium carbonate, iron carbonate, potassium carbonate and ammonium carbonate), hydrogen carbonate buffers which contain $HCO_3^-$ anion (e.g., sodium hydrogen carbonate, calcium hydrogen carbonate, ammonium hydrogen carbonate and potassium hydrogen carbonate).

In some embodiments, disclosed compositions can have a viscosity that renders them useful or deliverable as a sprayable composition. A composition can be sprayable via a non-pressurized dispenser or a pressurized pump dispenser, for example. In some embodiments, disclosed compositions can have a viscosity such that they are deliverable as a mist spray with a non-pressurized dispenser. In some embodiments, disclosed compositions can have a viscosity of not greater than 150,000 centipoise (cps), not greater than 100,000 cps, not greater than 50,000 cps, or not greater than 20,000 cps. In some embodiments, disclosed compositions can have a viscosity of not less than 2,500 centipoise (cps), not less than 5,000 cps, or not less than 7,500 cps.

In some embodiments, disclosed compositions are more viscous and can be delivered as a paste, spread, or pumpable lotion or cream. In some such embodiments, viscosities up to 2,000,000 cps can be potentially useful. In some embodiments, disclosed compositions can be a solid, or be emulsified in a solid. Some high viscosity sprays may also be delivered in other formats. In some specific illustrative embodiments, a lozenge format, a solid stick (e.g., lip balm), or other similar types of formats can be utilized.

In some embodiments, disclosed compositions can have desired stability properties. The stability of a composition can include microbiological stability, physical stability, or combinations thereof. In some embodiments, disclosed compositions are microbiologically stable for at least 6 months, in some embodiments 1 year, in some embodiments greater than 2 years.

In some embodiments, disclosed compositions remain physically stable when subjected to normal room temperature conditions, when subjected to temperatures approaching or surpassing the freezing point of the composition and subsequently thawed, or combinations thereof, for example. In some embodiments, the composition can be stable if it does remain physically stable when subjected to normal room temperature conditions, when subjected to temperatures approaching or surpassing the freezing point of the composition and subsequently thawed, or combinations thereof, for example. In some embodiments, disclosed compositions are physically stable when subjected to temperatures above room temperature, for example greater than 60° C. In some embodiments, disclosed compositions are physically stable when subjected to mechanical effects (e.g., gravitational) such as centrifugation, for example. In some embodiments, disclosed compositions are physically stable when subjected to both changes in temperature (such as those discussed above) and mechanical effects (such as those discussed above), for example. In some embodiments, a composition that is physically stable is one that does not separate into oil and water phases over the useful life of the product, during transport and/or storage, or any combinations thereof.

In some embodiments, disclosed compositions are physically stable when subjected to at least one freeze/thaw/centrifugation cycle. One freeze/thaw/centrifugation cycle includes freezing the composition (for a minimum of 3 hours for example), subsequently thawing the composition (for a minimum of 2 hours for example) and subsequently centrifuging the composition at 1750 rcf for 15 minutes. In some embodiments, disclosed compositions are physically stable when subjected to at least two freeze/thaw/centrifugation cycles, or at least three freeze/thaw/centrifugation cycles, for example. In some embodiments, disclosed compositions are physically stable when subjected to temperatures above 60° C., which can be referred to as one heat cycle. In some embodiments, disclosed compositions are physically stable when subjected to at least one heat cycle. In some embodiments, disclosed compositions are physically stable when subjected to at least one freeze/thaw/centrifugation cycle and subsequently one heat cycle.

In some embodiments, disclosed compositions can have desired effects when utilized. Such effects can include, for example the composition's effect on biofilms, the composition's effect on plaque buildup, the composition's effect on water loss, the composition's ability to maintain or provide lubricating properties, resist dilution or wash-off by saliva or water, or drinking and eating in general or combinations thereof.

In some embodiments, disclosed compositions can prevent, inhibit, disrupt, disperse, reduce the formation or maintenance of a biofilm in an area contacted with the composition. In some embodiments, a composition can prevent, inhibit, disrupt, disperse, reduce the formation or maintenance of a biofilm in a mouth of a user where the composition was applied to the mouth when compared to a mouth without the composition applied thereto. In some embodiments, a composition can prevent, inhibit, disrupt, disperse, reduce the formation or maintenance of a biofilm in a container in which a biofilm exists and the composition was applied to the container when compared to a container without the composition applied thereto. Preventing, inhibiting, disrupting, dispersing, reducing, controlling, or some combination thereof the formation or maintenance of biofilms can be measured using a modified version of the MBEC assay (described in ASTM E2799), which measures disruption of *Streptococcus mutans* biofilms grown on special pegs in a microtiter plate. The biofilms growing on the pegs are treated by periodic submersion into test materials, followed by washing in saliva and water. The biofilm remaining on each peg following treatment is quantified by measuring the amount of fluorescently labeled bacteria that eluted from the pegs at the end of the treatment cycles (see example). In some embodiments, disclosed compositions can affect the buildup of plaque in an area contacted by the composition. The area contacted can be in vivo or in vitro. In some embodiments, a composition can decrease plaque buildup on at least one tooth in a mouth of a user where the composition was applied to the mouth when compared to a mouth without the composition applied thereto. In some embodiments, a composition can decrease plaque buildup in a container in which plaque can develop and the composition was applied to the container when compared to a container without the composition applied thereto. Decreasing plaque buildup can be measured by a variety of methods in vivo including for example plaque scoring, dyeing of plaque, etc.

In some embodiments, disclosed compositions can affect hydration loss in an area contacted by the composition. The area contacted can be in vivo or in vitro. In some embodiments, a composition can decrease hydration loss in a mouth of a user where the composition was applied to the mouth when compared to a mouth without the composition applied thereto. In some embodiments, a composition can decrease hydration loss from a tissue in which hydration can be lost and the composition was applied to the tissue when compared to a tissue without the composition applied thereto. Hydration loss can be measured by exposing treated tissues of uniform size to a controlled 37° C. environment for a set time period (4 hrs), and recording the % weight loss from the treated tissue sample. The treated tissue is then exposed to high temperature to rid the sample of all water (95° C./4 hrs and 115° C./4 hrs). The water lost at 4 hrs is divided by the total water loss (after the 115° C. step) and is indicative of the water lost from the tissue at 4 hrs. In some embodiments, disclosed compositions can affect less than 65% water loss, or less than 60% water loss.

In some embodiments, disclosed compositions can affect lubricity or lubriciousness of an area contacted by the composition. The area contacted can be in vivo or in vitro. In some embodiments, a composition can maintain or increase lubricity in a mouth of a user where the composition was applied to the mouth when compared to a mouth without the composition applied thereto. In some embodiments, a composition can provide lubricating properties to a mouth to the same degree that saliva can, for example. In some embodiments, a composition can maintain or increase lubricity on a substrate in which lubricity can be lost and the composition was applied to the substrate when compared to a substrate without the composition applied thereto. Lubricity or the ability to provide lubricating properties can be measured by the friction coefficient relative to a suitable substrate. A low friction coefficient (comparable to saliva) is desired.

Disclosed compositions combine the benefits of oil and water phases. In some embodiments, disclosed compositions can combine numerous desired benefits such as lubrication, moisturization, exposure of hard tissue to beneficial minerals, and pH balancing. Finding an ingestible surfactant and thickening system to achieve all of the desired benefits required significant experimental investigation, was non-trivial, and required more than routine optimization. Furthermore, some disclosed compositions also achieve desired physical stability. Emulsions without certain physical stability criteria may have less than desirable product shelf life and commercial usefulness. Stability to freeze/thaw cycles may be important to ensure the emulsion is stable during storage and shipping. It may be commercially less desirable for an emulsion to be separated into water and oil phases before oral application. The unique combination of disclosed surfactants and thickening agents results in emulsion compositions that are physical stable to multiple cycles of freeze/thaw/centrifuge challenge testing and may be resistant to separation when exposed to elevated temperatures (>60° C.). Surprisingly some of these formulations also have anti-plaque property as demonstrated by in vitro anti-biofilm studies using *Streptococcus mutans*, a well-known biofilm-forming bacteria responsible for dental plaque.

Also disclosed herein are methods of using disclosed compositions. Disclosed methods can include contacting an oral cavity or oral tissue with a disclosed composition. The step of contacting the oral cavity or oral tissue can be accomplished by applying the composition in any way. Disclosed methods can be useful for preventing, inhibiting, disrupting, dispersing, reducing, controlling, or any combination thereof the formation or maintenance of a biofilm in an area contacted with the composition; for affecting hydration loss in an area contacted by the composition; for affecting lubricity or lubriciousness of an area contacted by the composition; for affecting or alleviating the effects of xerostomia, dry mouth, or both.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. For example, a composition that "comprises" silver may be a composition that "consists of" silver or that "consists essentially of" silver.

As used herein, "consisting essentially of," as it relates to a composition, apparatus, system, method or the like, means that the components of the composition, apparatus, system, method or the like are limited to the enumerated components and any other components that do not materially affect the basic and novel characteristic(s) of the composition, apparatus, system, method or the like.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Use of "first," "second," etc. in the description above and the claims that follow is not intended to necessarily indicate that the enumerated number of objects is present. For example, a "second" substrate is merely intended to differentiate from another substrate (such as a "first" substrate). Use of "first," "second," etc. in the description above and the claims that follow is also not necessarily intended to indicate that one comes earlier in time than the other.

Example articles and techniques according to the disclosure provide will be illustrated by the following non-limiting examples.

Examples

TABLE 1A

| Material | CAS# | Supplier |
|---|---|---|
| Mazola Oil | 8001-30-7 | Distributed by ACH Food Companies, INC. Memphis, TN 38016, USA |
| MEGA-9 (N-methyl-N-nonanoyl-D-glucamine) | 85261-19-4 | 3M, Saint Paul, MN 55144-1000 |
| MEGA-10 (N-methyl-N-decanoyl-D-glucamine) | 85261-20-7 | Sigma Aldrich; St. Louis, MO, USA |
| MEGA-8 (N-methyl-N-octanoyl-D-glucamine) | 85316-98-9 | Sigma Aldrich; St. Louis, MO, USA |
| N-Methyl Glucamine | 6284-40-8 | MP Biomedicals, Solon, OH, USA |
| Xylitol | 87-99-0 | Spectrum Chemical; New Brunswick, NJ, USA |
| Sucralose | 56038-13-2 | Sigma Aldrich; St. Louis, MO, USA |
| SpearMint | 8008-79-5 | Frutarom, Branchburg, NJ, USA |
| K2HPO4 | 7758-11-4 | Alfa Aesar, Tewksbury, MA 01876, USA |
| KH2PO4 | 7778-77-0 | BDH, Bristol, BS8 2BB, United Kingdom |
| CaHPO4 | 7757-93-9 | Spectrum Chemical; New Brunswick, NJ, USA |
| Thymol | 89-83-8 | Spectrum Chemical; New Brunswick, NJ, USA |
| GEOGARD ECT [benzyl alcohol (77-86%), salicylic acid (8-15%), glycerin (3-5%), and sorbic acid (1-4%)] | 100-51-6 69-72-7 56-81-5 110-44-1 | Lonza; South Plainfield, NJ, USA |

TABLE 1A-continued

| Material | CAS# | Supplier |
|---|---|---|
| Octyl Glucopyranoside | 29836-26-8 | Sigma Aldrich; St. Louis, MO, USA |
| N-Acetyl-D-Glucosamine | 7512-17-6 | Sigma Aldrich; St. Louis, MO, USA |
| N-Acetyl-D-Galactosamine | 14215-68-0 | MP Biomedicals, Solon, OH, USA |
| D-Glucosamine Hydrochloride | 66-84-2 | Sigma Aldrich; St. Louis, MO, USA |
| D-Glucosamine Sulfate | 29031-19-4 | MP Biomedicals, Solon, OH, USA |
| D-Glucamine | 488-43-7 | TCI, Portland, OR, USA |
| N-Methyl-D-Glucamine | 6284-40-8 | Alfa Aesar, Tewksbury, MA 01876, USA |
| N-Ethyl-D-Glucamine | 14216-22-9 | Fluka, Milwaukee, WI, USA |
| N-Octyl-D-Glucamine | 23323-37-7 | Carbosynth. Inc. Compton, Berkshire, RG20 6NE, UK |
| Xylitol | 87-99-0 | Spectrum Chemical; New Brunswick, NJ, USA |
| Sorbitol | 50-70-4 | Alfa Aesar, Tewksbury, MA 01876, USA |
| Erythritol | 149-32-6 | Cargill, Minneapolis, MN, USA |
| Mannitol | 69-65-8 | Mallinckrodt, Dublin, Ireland |
| Glycine | 56-40-6 | Sigma Aldrich; St. Louis, MO, USA |
| Arginine | 32042-43-6 | TCI, Portland, OR, USA |
| Nonanoic Acid | 112-05-0 | Alfa Aesar, Tewksbury, MA 01876, USA |
| Ethyl Caprylate | 106-32-1 | Sigma Aldrich; St. Louis, MO, USA |
| DMSO (Dimethyl sulfoxide) | 67-68-5 | Alfa Aesar, Tewksbury, MA 01876, USA |
| CHG (Chlorhexidine digluconate, 20% w/v aqueous solution) | 18472-51-0 | Alfa Aesar, Tewksbury, MA 01876, USA |
| NEOBEE 1053 (Medium Chain Triglycerides) | 73398-61-5 | Stepan Specialty Products, Northfield, IL, USA |
| Glycerin | 56-81-5 | Sigma Aldrich; St. Louis, MO, USA |

TABLE 1B

Commercially available products for treatment of xerostomia

| Product Name | BIOTENE Dry Mouth Oral Rinse | BIOTENE Moisturizing Mouth Spray | BIOTENE Oral Balance Gel |
|---|---|---|---|
| Manufacturer | GlaxoSmithKline Consumer Healthcare L.P., Moon Township, PA, USA | GlaxoSinithKline Consumer Healthcare L.P., Moon Township, PA, USA | GlaxoSmithKline Consumer Healthcare L.P., Moon Township, PA, USA |
| Ingredients | Purified Water, Propylene Glycol, Xylitol, Hydrogenated Starch Hydrolysate, Poloxamer 407, Hydroxyethylcellulose, Sodium Benzoate, Flavor (Peppermint Oil), Benzoic Acid, Disodium Phosphate, Zinc Gluconate, Lactoferrin, Lysozyme, Lactoperoxidase, Potassium | Purified Water, Glyercin, Xylitol, PEG-60 Hydrogenated Castor Oil, VP/VA Copolymer, Flavor, Sodium Benzoate, Xanthan Gum, Methylparaben, Propylparaben, Sodium Saccharin, Cetylpyridinium Chloride | Glycerin, water, sorbitol, xylitol, carbomer, hydroxyethyl cellulose, sodium hydroxide |

TABLE 1B-continued

Commercially available products for treatment of xerostomia

| Product Name | BIOTENE Dry Mouth Oral Rinse | BIOTENE Moisturizing Mouth Spray | BIOTENE Oral Balance Gel |
|---|---|---|---|
| | Thiocyanate, Aloe Vera Gel, Calcium Lactate, Glucose Oxidase. | | |
| Delivery Format | Oral Rinse | Spray mist | Tube |
| Viscosity Testing | Viscosity Results | Viscosity Results | Viscosity Results |
| sheer rate = 1/s Pa·s | NT | 4.523 | 108.00 |
| sheer rate = 3.16/s Pa·s | NT | 1.793 | 49.965 |
| sheer rate = 10/s Pa·s | NT | 0.726 | 24.390 |

TABLE 1C

Commercially available products for treatment of xerostomia

| Product Name | AQUORAL | LUBRICITY |
|---|---|---|
| Manufacturer | Mission Pharmacal Company; San Antonio, TX, USA | Lubricity Innovations Inc; Buffalo, NY, USA |
| Ingredients | 94.4% Oxidized glycerol triesters (OGT), silicon dioxide, aspartame, and artificial flavoring | Water, xylitol, hyaluronan, sodium benzoate, and potassium sorbate |
| Delivery Format | Spray jet | Spray mist |
| Viscosity Testing | Viscosity Results | Viscosity Results |
| sheer rate = 1/s Pa·s | NT | 0.198 |
| sheer rate = 3.16/s Pa·s | NT | 0.195 |
| sheer rate = 10/s Pa·s | NT | 0.186 |

Example Preparation Procedure

Example formulations were prepared in the following manner. The water phase components were mixed together by dissolving them all in water. This aqueous phase was stirred at room temperature (approximately 25° C.) for about 15 minutes to dissolve all the ingredients. Next, the oil was added to the prepared water phase while continuing to stir at room temperature for another 3 hours.

TABLE 4A

EXAMPLES EX.1-EX.5

| Example: Ingredient | EX.1 Wt % | EX.2 Wt % | EX.3 Wt % | EX.4 Wt % | EX.5 Wt % |
|---|---|---|---|---|---|
| Mazola Oil | 5.0 | 80.0 | 10.0 | 85.0 | 10.0 |
| Water | 45.0 | 5.0 | 80.0 | 7.0 | 7.0 |
| Glycerin | 47.0 | 12.0 | 7.0 | 5.0 | 80.0 |
| MEGA-9 | 0.7 | 0.7 | 0.7 | 0.7 | 0.7 |
| Methyl Glucamine | 0.5 | 0.5 | 0.5 | 0.5 | 0.5 |
| Xylitol | 1.0 | 1.0 | 1.0 | 1.0 | 1.0 |
| Sucralose | 0.15 | 0.15 | 0.15 | 0.15 | 0.15 |
| SpearMint | 0.35 | 0.35 | 0.35 | 0.35 | 0.35 |
| K2HPO4 | 0.155 | 0.155 | 0.155 | 0.155 | 0.155 |
| KH2PO4 | 0.076 | 0.076 | 0.076 | 0.076 | 0.076 |
| CaHPO4 | 0.0002 | 0.0002 | 0.0002 | 0.0002 | 0.0002 |
| Thymol | 0.1 | 0.1 | 0.1 | 0.1 | 0.1 |
| TOTAL | 100.0 | 100.0 | 100.0 | 100.0 | 100.0 |

TABLE 4B

EXAMPLES EX.6-EX.8

| Example: Ingredient | EX.6 Wt % | EX.7 Wt % | EX.8 Wt % |
|---|---|---|---|
| Mazola Oil | 82.47 | 82.47 | N/A |
| NEOBEE 1053 | N/A | N/A | 82.47 |
| Water | 14.5 | 14.5 | 14.5 |
| MEGA-9 | N/A | N/A | 0.7 |
| MEGA-10 | 0.7 | N/A | N/A |
| MEGA-8 | N/A | 0.7 | N/A |
| Methyl Glucamine | 0.5 | 0.5 | 0.5 |
| Xylitol | 1.0 | 1.0 | 1.0 |
| Sucralose | 0.15 | 0.15 | 0.15 |
| SpearMint | 0.35 | 0.35 | 0.35 |
| K2HPO4 | 0.155 | 0.155 | 0.155 |
| KH2PO4 | 0.076 | 0.076 | 0.076 |
| CaHPO4 | 0.0002 | 0.0002 | 0.0002 |
| Thymol | 0.1 | 0.1 | 0.1 |
| TOTAL | 100.0 | 100.0 | 100.0 |

TABLE 4C

EXAMPLES EX.9-EX.12

| Example: Ingredient | EX.9 Wt % | EX.10 Wt % | EX.11 Wt % | EX.12 Wt % |
|---|---|---|---|---|
| Mazola Oil | 82.47 | 72.47 | 62.47 | 52.47 |
| Glycerin | 0.0 | 10.0 | 20.0 | 30.0 |
| Water | 14.0 | 14.0 | 14.0 | 14.0 |
| MEGA-9 | 0.7 | 0.7 | 0.7 | 0.7 |
| Methyl Glucamine | 0.5 | 0.5 | 0.5 | 0.5 |
| Xylitol | 1.0 | 1.0 | 1.0 | 1.0 |
| Sucralose | 0.15 | 0.15 | 0.15 | 0.15 |
| SpearMint | 0.35 | 0.35 | 0.35 | 0.35 |
| K2HPO4 | 0.155 | 0.155 | 0.155 | 0.155 |
| KH2PO4 | 0.076 | 0.076 | 0.076 | 0.076 |
| CaHPO4 | 0.0002 | 0.0002 | 0.0002 | 0.0002 |
| GEOGARD ECT | 0.6 | 0.6 | 0.6 | 0.6 |
| TOTAL | 100.0 | 100.0 | 100.0 | 100.0 |

TABLE 4D

EXAMPLES EX.13-EX.16

| Example:<br>Ingredient | EX.13<br>Wt % | EX.14<br>Wt % | EX.15<br>Wt % | EX.16<br>Wt % |
|---|---|---|---|---|
| Mazola Oil | 42.47 | 32.47 | 22.47 | 12.47 |
| Glycerin | 40.0 | 50.0 | 60.0 | 70.0 |
| Water | 14.0 | 14.0 | 14.0 | 14.0 |
| MEGA-9 | 0.7 | 0.7 | 0.7 | 0.7 |
| Methyl Glucamine | 0.5 | 0.5 | 0.5 | 0.5 |
| Xylitol | 1.0 | 1.0 | 1.0 | 1.0 |
| Sucralose | 0.15 | 0.15 | 0.15 | 0.15 |
| SpearMint | 0.35 | 0.35 | 0.35 | 0.35 |
| K2HPO4 | 0.155 | 0.155 | 0.155 | 0.155 |
| KH2PO4 | 0.076 | 0.076 | 0.076 | 0.076 |
| CaHPO4 | 0.0002 | 0.0002 | 0.0002 | 0.0002 |
| GEOGARD ECT | 0.6 | 0.6 | 0.6 | 0.6 |
| TOTAL | 100.0 | 100.0 | 100.0 | 100.0 |

TABLE 4E

EXAMPLES EX.17-EX.18

| Example:<br>Ingredient | EX.17<br>Wt % | EX.18<br>Wt % |
|---|---|---|
| Mazola Oil | 80.0 | 78.0 |
| Water | 16.0 | 16.0 |
| MEGA-9 | 4.0 | 6.0 |
| Total | 100.0 | 100.0 |

Preparation of Aqueous Solution A

Aqueous Solution A was prepared as a stock solution used for the preparation of Examples EX. 19-EX. 23.

TABLE 4F

Aqueous Solution A

| Ingredient | Wt % |
|---|---|
| Water | 80.10 |
| Glycerin | 10.00 |
| MEGA-9 | 0.70 |
| Octyl Glucopyranoside | 0.70 |
| N-Acetyl-D-Glucosamine | 0.50 |
| N-Acetyl-D-Galactosamine | 0.50 |
| D-Glucosamine Hydrochloride | 0.50 |
| D-Glucosamine Sulfate | 0.50 |
| D-Glucamine | 0.50 |
| N-Methyl-D-Glucamine | 0.50 |
| N-Ethyl-D-Glucamine | 0.50 |
| N-Octyl-D-Glucamine | 0.50 |
| Xylitol | 0.50 |
| Sorbitol | 0.50 |
| Erythritol | 0.50 |
| Mannitol | 0.50 |
| Glycine | 0.50 |
| Arginine | 0.50 |
| Nonanoic Acid | 0.50 |
| Ethyl Caprylate | 0.50 |
| DMSO | 0.50 |
| TOTAL | 100.00 |

TABLE 4G

EXAMPLES EX.19-EX.23

| Example:<br>Water Phase | EX.19<br>grams | EX.20<br>grams | EX.21<br>grams | EX.22<br>grams | EX.23<br>grams |
|---|---|---|---|---|---|
| Aqueous Solution A | 5.0 | 6.0 | 7.0 | 8.0 | 9.0 |
| Mazola Oil | 40.0 | 40.0 | 40.0 | 40.0 | 40.0 |
| % Mazola Oil | 88.9% | 87.0% | 85.1% | 83.3% | 81.6% |

In-Vitro Hydration Retention Test Method (Thermogravimetric Analysis of Moisture Retention)

A LECO Thermogravimetric Analyzer (TGA) was used to determine the percentage weight loss of samples to simulate 4-hour hydration (moisture) retention in the oral cavity. In this in-vitro test, sliced, raw beef roast approximately 6 mm thick was used to mimic soft tissue. A circular biopsy punch of 1 cm diameter was taken from the raw roast beef slice to create disc-shaped tissue section samples. These samples were pre-weighed and then coated by immersing the tissue samples in one of the commercially available xerostomia alleviation products or example formulations. An uncoated beef sample was also analyzed as a control. Approximately 0.2 g of test material was weighed into a foil liner analysis container and placed into the LECO TGA Thermogravimetric Analyzer. The examples were then held at body temperature (37° C.) for 4 hours, and the percent (%) volatiles (water) lost after this step was recorded. Next, the temperature was increased to burn off all volatile materials and obtain the total weight fraction. The weight of lost after the 37° C. at the 4-hour step point was divided by the total volatiles, and expressed as a percentage (%) of total volatiles lost at 4 hours. The following table shows the details of the time/temperature profile used to run the program on the LECO TGA Thermogravimetric Analyzer.

TABLE 5

LECO TGA Program

| PARAMETER | Step 1 | Step 2 | Step 3 |
|---|---|---|---|
| Covers | No | No | No |
| Start Temp. ° C. | 25 | 37 | 95 |
| End Temp. ° C. | 37 | 95 | 115 |
| Ramp Rate | 1 | 5 | 1 |
| Ramp Time: hours:min | 00:12 | 00:11 | 00:20 |
| Hold Time: hours:min | 04:00 | 04:00 | 04:00 |
| Total Time: hours:min | 04:12 | 04:11 | 04:20 |
| Max Time: hours:min | 04:20 | 04:20 | 04:20 |
| Atmosphere | Air | Air | Air |
| Flow Rate | Medium | Med High | Med High |
| Window | 3 | 3 | 3 |

In-Vitro Hydration Retention Test Results Summary

Data for commercially available products and example formulations are summarized in the Tables 6A, 6B, and 6C below, which reflected three separate dates of analysis. Lower values are desirable for percent volatiles loss. Lower values for percent volatiles loss mean that the treatment formulation promotes more moisture retention, which is a desirable effect for a xerostomia treatment composition.

TABLE 6A

In-Vitro Hydration Retention Test Results

| Test Material | Step 1 37° C./4 hrs % wt loss | S.D. | Total % wt loss | S.D. | Ratio [Step 1/Total] |
|---|---|---|---|---|---|
| Beef Only | 50.1 (n = 3) | 2.9 | 69.5 | 1.4 | 0.72 |
| AQUORAL | 24.5 (n = 3) | 4.3 | 55.4 | 2.4 | 0.44 |
| BIOTENE Spray | 39.9 (n = 3) | 3.3 | 63.9 | 1.2 | 0.62 |
| EX.1 | 43.9 (n = 3) | 3.7 | 64.7 | 0.3 | 0.68 |
| EX.2 | 34.1 (n = 3) | 0.9 | 55.7 | 2.1 | 0.61 |
| EX.3 | 51.0 (n = 3) | 4.1 | 73.0 | 1.9 | 0.70 |
| EX.4 | 33.5 (n = 3) | 2.8 | 55.2 | 1.4 | 0.61 |
| EX.5 | 35.2 (n = 3) | 0.4 | 51.9 | 0.8 | 0.68 |
| EX.6 | 32.4 (n = 3) | 4.3 | 54.6 | 2.0 | 0.59 |
| EX.7 | 37.7 (n = 3) | 4.0 | 58.2 | 3.6 | 0.65 |
| EX.8 | 32.4 (n = 3) | 2.3 | 57.5 | 2.3 | 0.56 |
| EX.10 | 26.7 (n = 3) | 2.9 | 52.5 | 2.9 | 0.51 |
| EX.11 | 35.4 (n = 3) | 2.3 | 56.9 | 2.0 | 0.62 |
| EX.12 | 37.9 (n = 3) | 2.0 | 59.3 | 0.6 | 0.64 |
| EX.13 | 35.1 (n = 3) | 2.8 | 55.5 | 1.3 | 0.63 |
| EX.14 | 35.7 (n = 3) | 5.0 | 55.2 | 3.0 | 0.65 |
| EX.15 | 35.9 (n = 3) | 0.4 | 54.5 | 2.8 | 0.66 |
| EX.16 | 36.2 (n = 3) | 3.8 | 56.5 | 2.5 | 0.64 |

TABLE 6B

In-Vitro Hydration Retention Test Results

| Test Material | Step 1 37° C./4 hrs % wt loss | S.D. | Total % wt loss | S.D. | Ratio [Step 1/Total] |
|---|---|---|---|---|---|
| Beef Only | 54.1 (n = 3) | 3.3 | 65.9 | 3.4 | 0.82 |
| AQUORAL | 35.5 (n = 3) | 3.8 | 54.5 | 2.9 | 0.65 |
| BIOTENE Gel | 35.7 (n = 3) | 9.5 | 55.3 | 6.8 | 0.64 |
| EX.9 | 29.7 (n = 3) | 3.8 | 54.6 | 2.7 | 0.54 |

TABLE 6C

In-Vitro Hydration Retention Test Results

| Test Material | Step 1 37° C./4 hrs % wt loss | S.D. | Total % wt loss | S.D. | Ratio [Step 1/Total] |
|---|---|---|---|---|---|
| Beef Only | 56.3 (n = 3) | 2.5 | 71.3 | 0.7 | 0.79 |
| AQUORAL | 22.8 (n = 3) | 3.8 | 51.8 | 0.9 | 0.44 |
| EX.17 | 21.8 (n = 3) | 4.8 | 53.7 | 3.7 | 0.41 |

Viscosity Test Method

The viscosity of the Example formulations was measured at room temperature on an AR-G2 Magnetic Bearing Rheometer from TA Instruments Ltd., with parallel plate fixture. Approximately 1.4 mL of example formulation was placed between the plates and the gap of the plates was set to 1 mm for the measurement at room temperature. The viscosity was recorded at the shear rate of 1.0, 3.162, and 10 1/s. Two replicates for each formulation were conducted and the average was reported.

TABLE 7

Viscosity Test Results

| Example/Product | Ave. Viscosity (Pa · S) @ shear rate = 1 (1/s) | Ave. Viscosity (Pa · S) @ shear rate = 3.16 (1/s) | Ave. Viscosity (Pa · S) @ shear rate = 10 (1/s) |
|---|---|---|---|
| BIOTENE Spray | 4.52 | 1.79 | 0.73 |
| LUBRICITY | 0.27 | 0.25 | 0.23 |
| AQUORAL | 0.15 | 0.11 | 0.08 |
| Aqueous Solution A | 0.03 | 0.01 | 0.01 |
| EX.19 | 31.41 | 14.13 | 5.56 |
| EX.20 | 6.60 | 2.56 | 1.07 |
| EX.21 | 24.86 | 8.88 | 3.37 |
| EX.22 | 10.05 | 4.09 | 1.75 |
| EX.23 | 9.33 | 3.77 | 1.62 |

Friction Test Method:

Friction/Lubrication was measured using a FORCEBOARD universal friction tester (Industrial Dynamics, Sweden AB) affixed with a 10 newton (N) load cell. A natural lambskin condom made from sheep cecum (Trojan NATURALAMB™ Luxury Condoms, Church & Dwight Co., Inc. Ewing, N.J.) was used to mimic oral mucosal tissue. The condom was rinsed thoroughly and excess liquid was removed prior to use and between measurements to assure that no residual lubricant or example test formulation interfered with subsequent measurements. The condom was placed on a glass slide, smoothed to remove wrinkles, and clamped to the FORCEBOARD friction tester using a binder clip. A syringe was used to meter 0.5 ml of Example test solution (or other comparative samples such as water, or human saliva) onto the surface of the condom near the front of the FORCEBOARD (farthest from the motor). A second layer of condom was then secured around a gloved finger, and the covered finger was moved down the surface of the FORCEBOARD (toward the motor) while applying a target vertical force of 3 N. This motion was repeated 6-10 times for each replicate measurement. Friction coefficients (at a vertical force of 2.9 to 3.1 N) were calculated by the FORCEBOARD Analyzer software (Industrial Dynamics, Sweden). A low friction coefficient value is more slippery and thus is a desirable property for a formulation to treat xerostomia.

TABLE 8

Friction Test Results

| Product/Example | Friction Co-efficient (Average) | Standard Deviation |
|---|---|---|
| DI Water Control | 0.44 (n = 64) | 0.047 |
| BIOTENE Rinse | 0.19 (n = 99) | 0.008 |
| AQUORAL Spray | 0.19 (n = 87) | 0.023 |
| EX.1 | 0.28 (n = 95) | 0.033 |
| EX.2 | 0.26 (n = 94) | 0.035 |
| EX.3 | 0.34 (n = 40) | 0.033 |
| EX.4 | 0.27 (n = 75) | 0.039 |
| EX.5 | 0.25 (n = 53) | 0.038 |
| EX.6 | 0.22 (n = 49) | 0.026 |
| EX.7 | 0.25 (n = 58) | 0.019 |
| EX.8 | 0.26 (n = 82) | 0.041 |
| EX.10 | 0.28 (n = 70) | 0.039 |
| EX.11 | 0.29 (n = 50) | 0.036 |
| EX.12 | 0.21 (n = 85) | 0.046 |
| EX.13 | 0.25 (n = 45) | 0.051 |
| EX.14 | 0.26 (n = 42) | 0.028 |

TABLE 8-continued

Friction Test Results

| Product/Example | Friction Co-efficient (Average) | Standard Deviation |
|---|---|---|
| EX.15 | 0.25 (n = 74) | 0.035 |
| EX.16 | 0.31 (n = 75) | 0.055 |
| EX.17 | 0.21 (n = 70) | 0.004 |

Biofilm Disruption Test Method

This method utilizes the high throughput MBEC assay system (Innovotech, Calgary, AB Canada). The method evaluates efficacy of a treatment in disrupting biofilm by quantifying the amount of fluorescent-labeled biofilm remaining on MBEC inoculator pegs after exposure to relevant treatment conditions. The assay is similar to ASTM E2799-12 (*Standard Method for Testing Disinfectant Efficacy against Pseudomonas aeruginosa Biofilm using the MBEC™ Assay*) but was modified for use with *Streptococcus mutans* as the relevant organism and used a modified protocol for exposure of the biofilms to test materials.

MBEC Assay Procedure:

An overnight culture of *Streptococcus mutans* (ATCC 25175) was prepared by using a sterile inoculation loop to introduce a small amount of frozen stock into 5 mL of brain heart infusion (BHI) broth in a 15-mL conical tube. The tube was grown at 37° C. (static, not shaking) for 12-16 hours. The density of the overnight culture is estimated by turbidity measurement (OD600), and diluted appropriately to OD600=0.01 in BHI media supplemented with 1% sucrose and 1 uM Alexa Fluor® 488 dextran-10,000 MW (Molecular Probes® PN/D22910) to obtain an appropriate volume of inoculum to fill the required 96-well plate. 150 µL of inoculum is added to the appropriate wells of a 96 well MBEC™ Biofilm Inoculator plate (Innovotech® P&G Panel, polystyrene). The MBEC inoculator lid (with pegs positioned to be submerged in each well) is placed over the inoculated plate. The plate is wrapped in parafilm and incubated in a sealed plastic container humidified by lining the bottom of the plastic container with a wet paper towel (37° C., shaking at 250 RPM). A biofilm was allowed to form on the pegs for 4 hours prior to exposure of the biofilms to example formulation. In this modified assay, the biofilms growing on the pegs were exposed the example formulations 2 times during the assay, 7 and 18 hours post inoculum. The exposure to example formulations was performed as a treatment cycle with additional washing steps in and water. Treatment occurred by transferring the pegs into various 96-well plates filled with 150 CL/well of example formulations or 150 uL/well of water.

Treatment cycle steps (performed at 7 and 20 hours)
1) 1-minute exposure to test materials (150 UL/well)
2) 1-min rinse in water (200 CL/well)
3) 1-min rinse in water (200 CL/well)
4) 1-min rinse in water (200 CL/well)

After the water rinse, the pegs were returned to a 96 well plate filled with growth media (BHI+1% sucrose+1 µM Alexa Fluor® 488 dextran-10,000 MW) and returned to the incubator to allow for additional biofilm accumulation until the next treatment or until the end of the final growth period. Following the last treatment exposure cycle (at 20 hours post inoculation), the pegs were incubated in growth media for an additional 4 hours before transferring the MBEC pegs into a final wash plate for 1 minute (containing 150 µL sterile water per well, shaking at 37° C. for final rinsing), and then into a 96 well plate (black plate, suitable for fluorescence quantification in a plate reader) filled with 150 µL/well 50 U/mL dextranase (from *Penicillium* sp., Sigma® D4668-1KU) in 0.2M acetate, pH 5.5. The pegs were incubated in the extraction solution wells by shaking at 250 RPM at 37° C. for 30 minutes. The plate was then placed in a sonicating water bath for at least 1 hour at room temperature to elute the accumulated biofilm from the pegs into the dextranase/ acetate solution. Following sonication, the fluorescence in each well is read in a fluorescence plate reader (excitation=488 nm, emission=525 nm). Replicates of 4-8 wells per treatment were performed.

A control solution of 0.1% CHG (chlorhexidine gluconate) in water was prepared by diluting a 20% w/v CHG aqueous solution in water. This 0.1% CHG solution was also analyzed for biofilm disruption, as a comparative control solution.

Biofilm Disruption Test Method Results

Table 9 shows the average relative fluorescence reading for each example formulation treatment that was tested. A low value shows more biofilm disruption activity than a high value. Values are reported as relative fluorescence (%) normalized to the average fluorescence value for wells containing PBS as treatment negative control. For consistency, each MBEC plate was run with appropriate replication of PBS treatment wells. Data are normalized with PBS controls run in the same 96 well plate.

TABLE 9

Biofilm Disruption Test Results

| Sample | Fluorescence intensity of Alexafluor 488-labeled *S. mutans* biofilm matrix (arbitrary units: a.u.) | Standard Deviation | Normalized Relative Fluorescence (%) |
|---|---|---|---|
| PBS Control | 33672 | 7500 | 100% |
| 0.1% CHG | 1281 | 353 | 3.8% |
| Ex 11 | 1936 | 761 | 5.7% |

Illustrative Embodiments

1. A composition comprising:
from 0.1 wt-% to 8 wt-% of one or more compounds of formula (I) based on the total weight of the composition

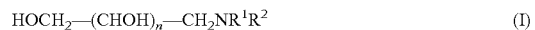

$$HOCH_2-(CHOH)_n-CH_2NR^1R^2 \qquad (I)$$

wherein $R^1$ and $R^2$ are independently selected from the group consisting of a hydrogen atom, an alkyl group, $C(O)R^3$, and $SO_2R^4$; with $R^3$ and $R^4$ being independently selected from the group consisting of an alkyl group, an aryl group, and an aralkyl group; wherein n is an integer from about 2 to about 5;

from 5 wt-% to 95 wt-% of one or more plant-based oils based on the total weight of the composition;

from 5 wt-% to 80 wt-% water based on the total weight of the composition, and from 0.01 wt.-% to 1 wt-% of one or more nonionic aromatic phenolic preservatives based on the total weight of the composition wherein the composition has a pH from 4.5 to 9.5, the composition is an emulsion, and the composition is edible.

2. The composition according to clause 1, wherein R1 and R2 are independently selected from the group consisting of a hydrogen atom, an alkyl group, and C(O)R3, wherein at least one of R1 and R2 is C(O)R3, R3 is selected from the group consisting of an alkyl group having seven carbon atoms, an alkyl group having eight carbon atoms, and an alkyl group having nine carbon atoms.

3. The composition according to any of clauses 1 to 2, wherein n is 4.

4. The composition according to any of clauses 1 to 3, wherein there is from 1 to 2 wt-% of formula I.

5. The composition according to clauses 2, wherein $R^3$ is an alkyl group having eight carbons.

6. The composition according to any of clauses 1 to 5, wherein the one or more edible plant based oils are selected from: sunflower oil, safflower oil, olive oil, coconut oil, palm oil, peanut oil, soybean oil, linseed oil, rapeseed oil, flaxseed oil, hempseed oil, cocoa butter, walnut oil, corn oil, grape seed oil, sesame oil, groundnut oil, wheat germ oil, cottonseed oil, fish oil, watermelon seed oil, lemon oil, orange oil, thistle oil, tomato seed oil, almond oil, perilla oil, canola oil, pistachio oil, hazelnut oil, camellia seed oil, shea nut oil, macadamia nut oil, apricot kernel oil, oleic acid, and avocado oil.

7. The composition according to any of clauses 1 to 6, wherein the one or more edible plant-based oils are from 75 wt-% to 95 wt-% based on the total weight of the composition.

8. The composition according to any of clauses 1 to 7, wherein the one or more nonionic aromatic phenolic preservative was selected from propyl paraben, thymol, a separate preservative mixture comprising 77-86%, benzyl alcohol, 8-15% salicylic acid, 3-5% glycerin and 1-4% sorbic acid, or combinations thereof.

9. The composition according to any of clauses 1 to 7, wherein the one or more nonionic aromatic phenolic preservative is present in an amount not greater than 0.8 wt-% based on the total weight of the composition.

10. The composition according to any of clauses 1 to 8, wherein the one or more nonionic aromatic phenolic preservative is present in an amount not greater than not greater than 0.6 wt-% based on the total weight of the composition.

11. The composition according to any of clauses 1 to 10 further comprising sweeteners, humectants, mineral salts, buffering components, flavorants, preservative agents, or combinations thereof.

12. The composition according to any of clauses 1 to 11 further comprising aloe vera, folic acid, hyaluronic acid, octyl glucopyranoside, N-acetyl-D-glucosamine, N-acetyl-D-Galactosamine, D-glucosamine hydrochloride, D-glucosamine sulfate, D-glucamine, N-methyl-D-glucamine, N-ethyl-D-glucamine, N-octyl-D-glucamine, xylitol, sorbitol, erythritol, mannitol, glycine, nonanoic acid, ethyl caprylate, DMSO, ceramides, arginine, betaines or oxygenated glycerol triesters, vitamin E, vitamin B12, EDTA, cetyl pyridinium chloride, chlorhexidine, other antiseptics, or combinations thereof.

13. The composition according to any of clauses 1 to 12, wherein the composition comprises from 1 wt-% to 20 wt-% sweeteners based on the total weight of the composition.

14. The composition according to any of clauses 1 to 13, wherein the composition comprises from 2.5 wt-% to 40 wt-% humectants based on the total weight of the composition.

15. The composition according to any of clauses 1 to 14, wherein the composition does not include any quaternary ammonium antimicrobial compounds.

16. The composition according to any of clauses 1 to 15, wherein the composition has a viscosity that renders it useful or deliverable as a sprayable composition.

17. The composition according to any of clauses 1 to 16, wherein the composition does not include any quaternary ammonium compounds.

18. The composition according to any of clauses 1 to 17, wherein the composition can prevent, inhibit, disrupt, disperse, reduce, control or any combination thereof the formation or maintenance of a biofilm in an area contacted with the composition.

19. The composition according to any of clauses 1 to 18, wherein the composition can affect hydration loss in an area contacted by the composition.

20. The composition according to any of clauses 1 to 19, wherein the composition can affect lubricity or lubriciousness of an area contacted by the composition.

21. A method of preventing, inhibiting, disrupting, dispersing, reducing, controlling, or any combination thereof the formation or maintenance of a biofilm in an oral tissue, the method comprising:
contacting an oral tissue with a composition according to any of clauses 1 to 20.

22. A method of affecting hydration loss in an oral tissue, the method comprising: contacting an oral tissue with a composition according to any of clauses 1 to 20.

23. A method of affecting lubricity or lubriciousness in an oral tissue, the method comprising:
contacting an oral tissue with a composition according to any of clauses 1 to 20.

24. The method of affecting the effects of xerostomia, dry mouth, or both, the method comprising:
contacting an oral tissue with a composition according to any of clauses 1 to 20.

Thus, embodiments of oral compositions and methods of use are disclosed. The implementations described above, and other implementations are within the scope of the following claims. One skilled in the art will appreciate that the present disclosure can be practiced with embodiments other than those disclosed. The disclosed embodiments are presented for purposes of illustration and not limitation.

What is claimed is:
1. A composition comprising:
one or more compounds of formula (I) present in an amount from 0.1 wt-% to 8 wt-% based on the total weight of the composition

wherein:
$R^1$ and $R^2$ are independently selected from the group consisting of hydrogen, an alkyl group, $C(O)R^3$, and $SO_2R^4$;
$R^3$ and $R^4$ being independently selected from the group consisting of an alkyl group, an aryl group, and an aralkyl group; and
n is an integer from 2 to 5;
one or more plant-based oils present in an amount from 75 wt-% to 95 wt-% of based on the total weight of the composition;
an aqueous phase comprising:
water,
wherein the aqueous phase is present in an amount no greater than 30 wt-% based on the total weight of the composition, and
one or more nonionic aromatic phenolic preservatives present in an amount from 0.01 wt-% to 1 wt-% based on the total weight of the composition wherein:
the composition is characterized by a pH from 4.5 to 9.5,
the composition is water-in-oil emulsion, and
the composition is edible.

2. The composition according to claim 1, wherein at least one of $R^1$ and $R^2$ is $C(O)R^3$, and $R^3$ is selected from the group consisting of a $C_{7-9}$ alkyl group.

3. The composition according to claim 1, wherein n is 4.

4. The composition according to claim 1, wherein a compound of formula I is present in an amount from 1 to 2 wt-%.

5. The composition according to claim 2, wherein $R^3$ is a $C_8$ alkyl group.

6. The composition according to claim 1, wherein the one or more edible plant-based oils are selected from: sunflower oil, safflower oil, olive oil, coconut oil, palm oil, peanut oil, soybean oil, linseed oil, rapeseed oil, flaxseed oil, hempseed oil, cocoa butter, walnut oil, corn oil, grape seed oil, sesame oil, groundnut oil, wheat germ oil, cottonseed oil, fish oil, watermelon seed oil, lemon oil, orange oil, thistle oil, tomato seed oil, almond oil, perilla oil, canola oil, pistachio oil, hazelnut oil, camellia seed oil, shea nut oil, apricot kernel oil, oleic acid, and avocado oil.

7. The composition according to claim 1, wherein the one or more nonionic aromatic phenolic preservative is selected from propyl paraben; thymol; a separate preservative mixture comprising 77-86%, benzyl alcohol, 8-15% salicylic acid, 3-5% glycerin and 1-4% sorbic acid; and a combination thereof.

8. The composition according to claim 1, wherein the one or more nonionic aromatic phenolic preservative is present in an amount not greater than 0.8 wt-% based on the total weight of the composition.

9. The composition according to claim 1, further comprising a sweetener, a humectant, a mineral salt, a buffering component, a flavorant, a preservative agent, or a combination thereof.

10. The composition according to claim 1, further comprising aloe vera, folic acid, hyaluronic acid, octyl glucopyranoside, N-acetyl-D-glucosamine, N-acetyl-D-Galactosamine, D-glucosamine hydrochloride, D-glucosamine sulfate, D-glucamine, N-methyl-D-glucamine, N-ethyl-D-glucamine, N-octyl-D-glucamine, xylitol, sorbitol, erythritol, mannitol, glycine, nonanoic acid, ethyl caprylate, DMSO, ceramides, arginine, betaines or oxygenated glycerol triesters, vitamin E, vitamin B12, EDTA, cetyl pyridinium chloride, chlorhexidine, other antiseptics, or a combination thereof.

11. The composition according to claim 1, further comprising a sweetener present in an amount from 1 wt-% to 20 wt-% based on the total weight of the composition.

12. The composition according to claim 1, further comprising a humectant present in an amount from 2.5 wt-% to 40 wt-% based on the total weight of the composition.

13. The composition according to claim 1, wherein the composition does not include any quaternary ammonium antimicrobial compounds.

14. The composition according to claim 1, wherein the composition one or more of prevents, inhibits, disrupts, disperses, reduces, and controls the formation or maintenance of a biofilm in an area contacted with the composition.

15. The composition according to claim 1, wherein the composition reduces hydration loss in an area contacted by the composition.

16. The composition according to claim 1, wherein the composition increases lubricity or lubriciousness of an area contacted by the composition.

17. A method of reducing hydration loss in an oral tissue, the method comprising:
contacting an oral tissue with a composition according to claim 1.

18. A method of increasing lubricity or lubriciousness in an oral tissue, the method comprising:
contacting an oral tissue with a composition according to claim 1.

19. A method of mitigating the effects of xerostomia, dry mouth, or both, the method comprising:
contacting an oral tissue with a composition according to claim 1.

* * * * *